United States Patent [19]
Osteryoung

[11] Patent Number: 5,981,836
[45] Date of Patent: Nov. 9, 1999

[54] PLANT PLASTID DIVISION GENES

[75] Inventor: Katherine W. Osteryoung, Reno, Nev.

[73] Assignee: The University of Nevada, Reno, Nev.

[21] Appl. No.: 08/883,515

[22] Filed: Jun. 26, 1997

Related U.S. Application Data

[60] Provisional application No. 60/020,959, Jun. 28, 1996.

[51] Int. Cl.$^6$ .............................. C12N 15/29; C12N 5/04; C12N 15/82; A01H 5/00
[52] U.S. Cl. ..................... 800/278; 536/23.1; 536/23.6; 435/69.1; 435/70.1; 435/71.1; 435/468; 435/419; 435/320.1; 435/410; 800/278; 800/282; 800/290; 800/293; 800/294; 800/295; 800/298; 800/306
[58] Field of Search .................................. 536/23.6, 23.1; 800/205, DIG. 15, 278, 282, 290, 293, 294, 295, 298, 306; 435/69.1, 440, 468, 410, 419, 70.1, 71.1, 320.1

[56] References Cited

PUBLICATIONS

Gleave, Andrew P., "A versatile binary vector system with a T–DNA organisational structure conducive to efficient integration of cloned DNA into the plant genome," *Plant Molecular Biology*, 20:1203–1207 (1992).

Lutkenhaus, Joe, "FtsZ ring in bacterial cytokinesis," *Molecular Microbiology* 9(3):403–409 (1993).

Osteryoung, Katherine W., et al., "Conserved cell and organelle division," *Nature*, 376:473–474 (Aug. 10, 1995).

Pyke, Kevin A., et al., "arc6, A Fertile Arabidopsis Mutant with Only Two Mesophyll Cell Chloroplasts," *Plant Physiol.*, 106:1169–1177 (1994).

Pyke, Kevin A., et al., "Rapid Image Analysis Screening Procedure for Identifying Chloroplast Number Mutants in Mesophyll Cells of *Arabidopsis thaliana* (L.) Heynh," *Plant Physiol.*, 96:1193–1195 (1991).

Pyke, Kevin A., et al., "Chloroplast Division and Expansion Is Radically Altered by Nuclear Mutations in *Arabidopsis thaliana*," *Plant Physiol.*, 99:1005–1008 (1992).

Robertson, E.J., et al., "arc6, an extreme chloroplast division mutant of Arabidopsis also alters proplastid proliferation and morphology in shoot and root apices," *Journal of Cell Science*, 108:2937–2944 (1995).

Robertson, Elizabeth J., et al., "Characterization of Chloroplast Division Using the Arabidopsis Mutant arc5," *Plant Physiol.*, 112:149–159 (1996).

Suzuki, Kuninori, et al., "Behavior of mitochondria, chloroplasts and their nuclei during the mitotic cycle in the ultramicroalga Cyanidiioschyzon merolae," *European Journal of Cell Biology*, 63:280–288 (1994).

Napoli et al. The Plant Cell. 1989. vol. 2: 278–289.

Zhang et al. The Plant Cell. 1992. vol. 4: 1575–1588.

Baertlein et al. Plant Physiol. 1992. vol. 100: 1730–1736.

Reiter et al. The Plant Cell. 1994, vol. 6: 1253–1264.

*Primary Examiner*—Lynette R. F. Smith
*Assistant Examiner*—Ousama M-Fait Zaghmout
*Attorney, Agent, or Firm*—Quarles & Brady LLP

[57] ABSTRACT

Disclosed are DNA sequences that play a critical role in regulating plastid division in plants. Also disclosed is a method for obtaining transgenic plants with novel phenotypes, characterized by alterations in plastid number and size.

17 Claims, 6 Drawing Sheets

| | | | | | | |
|---|---|---|---|---|---|---|
| B. subtilis | ........... | ........... | ........... | ........... | ..........M | LEFETNIDG. | 10 |
| S. aureus | ........... | ........... | ........... | ........... | ..........M | LEFEQGFNH. | 10 |
| Anabaena | ........... | ...MTLDNN | QELTYRNSQS | LGQPGFSLAV | NSSNPFNHSG | LNFGQNNDSK | 46 |
| AtFtsZ | DPRVRVVAAQ | KSESSPIRNS | PRHYQSQAQD | PFLNLHPEIS | MLRGEGTSTI | VNPRKETSSG | 60 |
| cpFtsZ | ..MAIIPLA | QLNELTISSS | SSSFLTKSIS | .SHSLHSSCI | CASSRISQFR | GGFSKRRSDS | 56 |
| E. coli | ........... | ........... | ........... | ........... | ........... | ........... | |
| R. meliloti | ........... | ........... | ........... | ........... | ........... | ........... | |
| Consensus | | | | | | | |
| B. subtilis | ........... | ......LASI | KVIGVGGGGN | NAVNRMIENE | VQGVEYIAVN | TDAQALNLSK | 54 |
| S. aureus | ........... | ......LATL | KVIGVGGGGN | NAVNRMIDHG | MNNVEFIAIN | TDGQALNLSK | 54 |
| Anabaena | KISVENNRIG | EIVPGRVANI | KVIGVGGGGG | NAVNRMIESD | VSGVEFWSIN | TDAQALTLAG | 106 |
| AtFtsZ | PVVEDFEEPS | APSNYNEARI | KVIGVGGGGS | NAVNRMIESE | MSGVEFWIVN | TDIQAMRMSP | 120 |
| cpFtsZ | TRSKSMRLRC | SFSPMESARI | KVIGVGGGGN | NAVNRMISSG | LQSVDFYAIN | TDSQA..LLQ | 114 |
| E. coli | .....MFE | PMELTNDAVI | KVIGVGGGGG | NAVEHMVRER | IEGVEFFAVN | TDAQALRKTA | 53 |
| R. meliloti | ...MTEYKK | PIITEMRPKI | TVIGVGGGGG | NAINNMIAEN | LQGVDFIAAN | TDAQALATSK | 56 |
| Consensus | | | VIGVGGGG | NA M | V | TD QA | |
| B. subtilis | ..AEVKMQIG | AKLITRGLGAG | ANPEVGKKAA | EESKEQIEEA | LKGADMVFVT | AGMGGGTGTG | 112 |
| S. aureus | ..AESKIQIG | EKLITRGLGAG | ANPEIGKKAA | EESREQIEDA | IQGADMVFVT | SGMGGGTGTG | 112 |
| Anabaena | ..APSRLQIG | QKLITRGLGAG | GNPAIGQKAA | EESRDEIATA | LEGADLVFIT | AGMGGGTGTG | 164 |
| AtFtsZ | VLPDNRLQIG | KELTRGLGAG | GNPEIGMNAA | RESKEVIEEA | LYGSDMVFVT | AGMGGGTGTG | 180 |
| cpFtsZ | FSAENPLQIG | ELLTRGLGTG | GNPLLGEQAA | EESKDAIANA | LKGSDLVFIT | AGMGGGTGSG | 174 |
| E. coli | ..VGQTIQIG | SGITKGLGAG | ANPEVGRNAA | DEDRDALRAA | LEGADMVFIA | AGMGGGTGTG | 111 |
| R. meliloti | ..AERRIQLG | AAITEGLGAG | SVPDIGNAAA | QESIDEIMDH | LGGTHMCFVT | AGMGGGTGTG | 114 |
| Consensus | Q G | T GLG G | P G AA | E | G F | GMGGGTG G | |

FIG 1

```
B. subtilis   AAPVIAQIAK DLGALTVGVV TRPFTFEGRK RQLQAAGGIS AMKEAVDTLI VIPNDRILEI   172
S. aureus     AAPVVAKIAK EMGALTVGVV TRPFSFEGRK RQTQAAAGVE AMKAAVDTLI VIPNDRLLDI   172
Anabaena      AAPIVAEVAK EMGALTVGVV TRPFVFEGRR RTSQAEQGIE GLKSRVDTLI IIPNNKLLEV   224
AtFtsZ        AAPVIAGIAK AMGILTVGIA TTPFSFEGRR RTVQAQEGLA SLRDNVDTLI VIPNDKLLTA   240
cpFtsZ        AAPVVAQISK DAGYLTVGVV TYPFSFEGRK RSLQALEAIE KLQKNVDTLI VIPNDRLLDI   234
E. coli       AAPVVAEVAK DLGILTVAVV TKPFNFEGKK RMAFAEQGIT ELSKHVDSLI TIPNDKLLKV   171
R. meliloti   AAPVIAEAAR RAGILTVAVV TKPFSFEGQR RMQTAELGVE RLRESADTVI VIPNQNLFRI   174
Consensus     AAP A              G LTV        T PF FEG   R   A           D I    IPN B. subtilis   VDKNTPMLEA FREADNVLRQ GVQGISDLIA TPGLINLDFA DVKTIMSNKG SALMGIGIAT   232
S. aureus     VDKSTPMMEA FKEADNVLRQ GVQGISDLIA VSGEVNLDFA DVKTIMSNQG SALMGIGVSS   232
Anabaena      IPEQTPVQEA FRYADDVLRQ GVQGISDIIT IPGLVNVDFA DVRAVMADAG SALMGIGVSS   284
AtFtsZ        VSQSTPVTEA FNLADDILRQ GVRGISDIIT IPGLVNVDFA DVRAIMANAG SSLMGIGTAT   300
cpFtsZ        ADEQTPLQDA FLLADDVLRQ GVQGISDIIT IPGLVNVDFA DVKAVMKDSG TAMLGVGVSS   294
E. coli       LGRGISLLDA FGAANDVLKG AVQGIAELIT RPGLMNVDFA DVRTVMSEMG YAMMGSGVAS   231
R. meliloti   ADAKTTFADA FMIADRVLYS GVSCITDLIV KEGLMNLDFA DVKTVMKGMG RAMMGTGEAT   234
Consensus                A   F A  A      PL       AG     I  V I I   G  N DFA DV   M   G       G G B. subtilis   GENRAEEAAK KAISSPLL.E AAIDGAQGVL MNITGGTNLS LYEVQEAADI VASASDQDVN   291
S. aureus     GENRAVEAAK KAISSPLL.E TSIVGAQGVL MNITGGESLS LFEAQEAADI VQDAAEDDVN   291
Anabaena      GKSRAREAAI AAISSPLL.E CSIEGARGVV FNITGGSDLT LHEEVNAAAET IYEVVDPNAN   343
AtFtsZ        GKSRARDAAL NAIQSPLL.D IGIERATGIV WNITGGSDLT LFEVNAAAEV IYDLVDPTAN   359
cpFtsZ        SKNRAEEAAE QATLAPLI.G SSIQSATGVV YNITGGKDIT LQEVNRVSQV VTSLADPSAN   353
E. coli       GEDRAEEAAE MAISSPLLED IDLSGARGVL VNITAGFDLR LDEFETVGNT IRAFASDNAT   291
R. meliloti   GENRAMLAAE AAIANPLLDE VSMRGAKGVL VSISGGMDMT LFEVDEAATR IREEVYDEAD   294
Consensus     RA  AA       A   PL       AG            I G              L E
```

FIG 1

```
B. subtilis    MIFGSVINEN  LKDEIVVTVI  ATGFIEQ.EK  DVTKPQ..RP  SLNQSIKTHN  QSVPKRD...     345
S. aureus      MIFGTVINPE  LQDEIVVTVI  ATGFDDKPTS  HGRKSG..ST  GFGTSVNTSS  NATSKDESFT     349
Anabaena       IIFGAVIDDR  LQGEVRITVI  ATGFTG..EI  QAAPQQ..NA  ANARVVAAPP  KRTPTQTPLT     399
AtFtsZ         LIFGAVVDPA  LSGQVSITLI  ATGFKRQEEG  EGRTVQMVQA  DAASVGATRR  PSSSFRES..     417
cpFtsZ         IIFGAVVDDR  YTGEIHVTII  ATGFSQSFQ.  ...KTLLTDP  RAAKLLDKMG  SSGQQENKGM     410
E. coli        VVIGTSLDPD  MNDELRVTVV  ATGIGMDKRP  EITLVT..NK  QVQQPVMDRY  QQHGM.APLT     348
R. meliloti    IVVGAIFDRS  LDGTFRVS.V  ATGLDSNRSA  QPTAPEAMNG  QTAAAVPSRT  LQ........     345
Consensus                              ATG B. subtilis    AKREEPQQQN  TVSRHTSQPA  DDTLDIPTFL  RNRNKRG...  ...            382
S. aureus      SNSSNAQATD  SVSERTHTTK  ED..DIPSFI  RNREERRSRR  TRR            390
Anabaena       NSPAPTPEPK  EKS.......  ..GLDIPDFL  QRRRPPKN..  ...            428
AtFtsZ         ..........  ..........  .GSVEIPEFL  KKKGSSRYPR  V..            437
cpFtsZ         SLPHQKQSPS  TISTKSSSPR  RLFF......  ..........  ...            433
E. coli        QEQKPVAKVV  NDNAPQTAKE  PDYLDIPAFL  RKQAD.....  ...            383
R. meliloti    ..........  ..........  ..........  ..........  ...            345
Consensus
```

100 ## PLANT PLASTID DIVISION GENES

CROSS-REFERENCE TO RELATED APPLICATIONS

This application claims priority from provisional patent application Ser. No. 60/020,959 filed Jun. 28, 1996.

STATEMENT REGARDING FEDERALLY SPONSORED RESEARCH OR DEVELOPMENT

Not applicable.

BACKGROUND OF THE INVENTION

The agriculture industry has devoted considerable resources toward the development of phenotypically distinct plants with economically advantageous qualities. Valuable features in food crops include increased vigor, disease resistance, greater yields, extended shelf-life, and enhanced nutritional content.

The development of high yielding food crops is particularly important. Each year, the tillable land available for agricultural production is reduced as more acreage is devoted to alternative uses. At the same time, the human population is rapidly increasing. Therefore, it is essential to increase agricultural productivity in order to meet the nutritional needs of the world's burgeoning population.

Efforts to develop crop plants that produce higher yields have been directed toward pest control, or toward the selection and breeding of varieties that bear greater numbers of fruit, or that produce larger fruit. These crop breeding endeavors are very time-consuming and labor-intensive, but have historically increased crop yields incrementally over time. Modern techniques of recombinant DNA manipulation and genetic engineering offer the prospect of the more rapid creation of new plant varieties with novel traits.

Photosynthesis in plants is a critically important biosynthetic process upon which virtually all living organisms depend for our very existence. Photosynthesis occurs in the chloroplasts of plant cells. In the process of photosynthesis, energy in the form of light is converted to ATP, which fuels a series of enzymatic reactions that catalyze the synthesis of carbohydrates. Molecular oxygen ($O_2$) is an essential byproduct of photosynthesis. Since photosynthesis is the source of metabolic energy in plants, photosynthetic efficiency is a significant factor associated with general plant growth and vigor.

It is known that photosynthetic activity is positively correlated with chloroplast number (Leech and Baker, "The development of photosynthetic capacity in leaves. In: J. E. Dale and F. L. Milthorpe (eds), The Growth and Functioning of Leaves. Cambridge University Press, Cambridge. pp 271–307, 1983). Despite the centrality of the photosynthetic function of chloroplasts to life, relatively little is known about the manner in which chloroplast number and size are regulated.

Chloroplasts are also the site of several important biochemical processes in plant cells that contribute to nutritional content of CRO plant. Amino acids and lipids are synthesized in chloroplasts. Plastids are also the site of synthesis of some important secondary metabolites and vitamins.

What is needed in the art is a means for manipulating the number and size of chloroplasts in agronomically and horticulturally important plants to achieve greater plant productivity and nutritional quality.

BRIEF SUMMARY OF THE INVENTION

The present invention is a plant comprising in its genome a genetic construct comprising a plastid division sequence and a promoter, not natively associated with the gene, which promotes expression of the gene in the plant, wherein expression of the gene in the plant causes alterations in the number and size of plastids in plant cells of the plant.

The present invention is also two DNA sequences (SEQ ID NO:1 and SEQ ID NO:3) representing one type of gene that functions in regulating plastid division, and which, when ectopically expressed, alter the number and size of chloroplasts and other types of plastids present in plant cells.

The present invention is directed toward a genetic construct comprising a plastid division sequence and a promoter that promotes expression of the sequence in plants, the promoter not being natively associated with the plastid division sequence.

The present invention is also a seed, comprising in its genome a genetic construct comprising a plastid division sequence and a promoter, not natively associated with the plastid division sequence, that promotes gene expression in plants.

The present invention is also a plant cell comprising in its genome a genetic construct comprising a plastid division sequence and a promoter, not natively associated with the plastid division sequence, that promotes gene expression in plants.

It is an object of the present invention to provide a transgenic plant that has a novel phenotype with advantageous qualities, including increased numbers of chloroplasts.

Other objects, advantages, and features of the present invention will become apparent after review of the specification and drawings.

DETAILED DESCRIPTION OF THE INVENTION

One aspect of the present invention is a plant that contains in its genome a genetic construct comprising a plant plastid division gene sequence and a promoter, not natively associated with the plastid division gene, which promotes expression of the gene in plants. Transgenic expression of the gene results in a high percentage of novel phenotypes characterized by alterations in the number and size of plastids in cells of the plant in which the construct is expressed.

Plastids are a membrane-delimited organelles of plant cells that are essential for plant cell viability. It is in the specialized plastid chloroplast that photosynthesis occurs. Plastids are the site of the synthesis of essential amino acids, vitamin E, pro-vitamin A, starch, certain growth hormones, lipids, and pigments such as carotenes, xanthophylls, and chlorophylls. Because plastids are essential for plant cell viability, the regulation of plastid division is a critical function. To ensure that each newly-divided cell contains the plastids essential for viability, plastids must be replicated during the cell cycle and portioned at cell division.

Depending on the species, the number of chloroplasts per cell in leaves increases from fewer than 15 proplastids in leaf primordia to more than 150 chloroplasts in mature, photosynthetically competent mesophyll cells. Developmental patterns of chloroplast division have been characterized in both monocots and dicots. In monocots, newly formed leaf cells arise from an intercalary meristem at the base of the leaf, giving rise to bands of cells that form a linear developmental gradient from the base to the tip of the leaf. A cross-section through a particular part of the leaf therefore yields a population of cells at the same developmental stage. Leaf growth at the base of the wheat leaf in the meristem occurs by cell division, whereas above the meristem, cell division ceases and leaf growth occurs strictly by cell expansion. The number of chloroplasts per cell remains constant in meristematic cells, indicating that chloroplasts division keeps pace with cell division at this stage of development. The major increase in chloroplast number occurs during cell expansion (Leech and Pyke, "Chloroplast division in higher plants with particular reference to wheat." In S. A. Boffey and D. Lloyd (eds) *Division and Segregation of Organelles*. Cambridge University Press, Cambridge, pp. 39–62, 1988).

The pattern of leaf development in dicots is more complex, but in general parallels that in monocots. Growth occurs primarily by division for very young cells at the base of the leaf, and by expansion for mature cells above the base. As in monocots, examination of dicot leaf cross-sections demonstrated the number of chloroplasts per cell in dicots changes little in immature dividing cells near the leaf base, but increases in expanding cells with increasing distance from the base. The pattern of chloroplast division is also reflected in an increase in the average numbers of chloroplasts in progressively older leaves. For example, in spinach, leaves 2 cm in length average fewer than 20 chloroplasts per cell, while fully expanded leaves 10 cm in length average more than 150 chloroplasts per cell. (Lawrence, et al. *Plant Physiol.* 91:708–710, 1986). In general, these studies indicate that there is a developmentally controlled increase in chloroplast number (or chloroplast divisions) per cell as the leaf matures.

Arabidopsis arc (accumulation and replication of chloroplasts) mutants, identified by microscopic examination of populations of EMS-mutagenized and T-DNA-mutagenized plants, exhibit large changes in the number and size of chloroplasts relative to wild-type (Pyke, et al. *Plant Physiol.* 104:201–207, 1994, Pyke, et al. *Plant Physiol.* 99:1005–1008, 1992). Mutants exhibiting both reduced and increased numbers of chloroplasts per unit mesophyll cell area have been identified. Surprisingly, the growth of the arc mutants is not impaired (Pyke, et al. *Plant Physiol.* 104:201–207, 1994, Pyke, et al. *Plant Physiol.* 99:1005–1008, 1992), or is impaired no more than 30% in the most severe mutant, arc6, which has on average only two chloroplasts per cell, as compared with 83 in wild-type (Pyke, et al. *Plant Physiol.* 106:1169–1177, 1994; Pyke, et al. *J. Cell Sci.* 108:29372944, 1994). Flowering, fertility, and seed set are normal in all arc mutants.

In examining the relationship between chloroplast number and size in arc mutants, it was determined that changes in chloroplast number are closely compensated for by inversely related changes in chloroplast size, such that total chloroplast volume per unit cell volume is comparable in mutants and wild-type plant cells (Pyke, et al. *Plant Physiol.* 99:1005–1008, 1992). These data indicate that plastid division and plastid expansion are genetically distinct processes which are integrated via a feedback mechanism that senses total chloroplast compartment size. Similarly, as detailed in the examples below, an alteration in the number of chloroplasts that results from expression of chloroplast division genes inserted as transgenes also causes compensatory changes in chloroplast size.

The ability to alter the expression of the chloroplast division genes allows the manipulation of the size and number of chloroplasts in plant cells. Chloroplast number is known to have a direct effect on photosynthetic capacity (Leech and Baker, "The development of photosynthetic capacity in leaves. In: J. E. Dale and F. L. Milthorpe (eds), *The Growth and Functioning of Leaves*. Cambridge University Press, pp 271–307, 1983). It is therefore likely that by manipulating levels of plastid division proteins in genetically engineered plants to achieve increased numbers or size of plastids, which play a critical role in plant biosynthetic processes, one may obtain plants having advantageous properties. As an example of the utility of this invention, one may use the invention to develop agronomically and horticulturally important plants with enhanced vigor and productivity, or with enhanced production of one or more of the various compounds that are synthesized in plastids.

The identification and characterization of two *Arabidopsis thaliana* plastid division sequences that are useful in the present invention are described in the examples below. The sequences, designated cpFtsZ (cp for chloroplast, SEQ ID NO:1) and AtFtsZ (At for *Arabidopsis thaliana*, SEQ ID NO:3) were identified on the basis of homology to bacterial FtsZ genes, which have been isolated from Fts (filamenting temperature-sensitive) strains of several prokaryotic species. Bacterial Fts mutants have a temperature-sensitive mutation in a gene that is involved in bacterial cell division; these mutants form bacterial filaments due to incomplete septum formation during cell division.

The bacterial cell division protein FtsZ is a key component of the bacterial cell division machinery. It assembles into a cytokinetic ring at the onset of division, and disassembles after septation is completed. A cytoskeletal role for FtsZ in bacterial cell division has been postulated based on its ability to undergo GTP-dependent polymerization in vitro, and on other structural similarities to tubulin. As shown in the examples below, the Arabidopsis FtsZ proteins contain a glycine-rich tubulin signature motif which is conserved among FtsZ proteins and tubulins, and which is important for GTP binding, which suggests that the proteins may have a cytoskeletal role analogous to that of tubulin.

As used herein, "FtsZ" refers to the Arabidopsis cpFtsZ and AtFtsZ sequences, as well as the analogous gene sequences from other plants as well as variations and mutants thereof which retain plastid division control functionality. As shown in the examples below, the FtsZ genes are highly conserved among diverse plant species. It is expected that all plants contain plastid division genes homologous to the Arabidopsis plastid division genes cpFtsZ or AtFtsZ. The bacterial FtsZ genes are also homologous to these plant FtsZ genes and might be used as well in transgenic plants.

Given the apparent ubiquitousness and high degree of conservation of plastid division sequences among plant species, it is reasonable to expect that plastid division genes, of which the FtsZ gene is but one example, from any plant could be used in the practice of the present invention. For example, plants that are raised for their agricultural or horticultural value may be used in the practice of the present invention.

It is specifically contemplated that any plastid division sequence could be used in the practice of the present invention. By a "plastid division sequence" is meant any plant DNA sequence which exhibits plastid division activity. A plastid division sequence may be an unmodified sequence isolated from any plant, a cDNA sequence derived from any plant, a genomic or cDNA sequence that is modified to contain minor nucleotide additions, deletions, or substitutions, or a synthetic DNA sequence. The term is intended to apply, as well, to analogous sequences from other plants as well as allelic variations and mutations which are still capable of controlling plastid division.

By "plastid division activity" is meant the ability to cause alterations in the number or size of the chloroplast or other types of plastids present in cells of a transgenic plant in which the plastid division sequence is expressed.

By "transgene" it is meant to describe an artificial genetic construction carried in the genome of a plant and inserted in the plant or its ancestor by gene transfer. Such transgenes are transmissible by normal Medellian inheritance once inserted.

It is specifically envisioned that transgenic plants can be made with a transgene for a plastid division sequence which selectively either up-regulates or down-regulates plastid division activity. For more plastid divisions, extra copies or high expression copies of plastid division sequences transgenes are inserted into plants. For less plastid division, the use of an antisense plastid division sequence transgene, or any other gene inhibition technique, may be used to down regulate plastid divisions. Both up and down regulation of plastids will be useful for certain applications. Transgenic Arabidopsis plants were obtained as a model system using the Agrobacterium transformation system, as described in the examples. Agrobacterium-mediated transformation is known to work well with many dicot plants and some monocots. Other methods of transformation equally useful in dicots and monocots may also be used in the practice of the present invention. Transgenic plants may be obtained by particle bombardment, electroporation, or by any other method of transforming plants known to one skilled in the art of plant molecular biology. The experience to date in the technology of plant genetic engineering is that the method of gene introduction is not of particular importance in the phenotype achieved in the transgenic plant.

The present invention is also directed toward a genetic construct comprising a plastid division sequence and a promoter, not natively associated with the sequence, which promotes expression of the plastid division sequence in plants at levels sufficient to cause novel phenotypes. The construct may contain the sequence in either the sense or antisense orientation. The development of three constructs that have been found to alter the number or size of chloroplasts in transformed plant cells is described in the examples. Briefly, relevant features of these constructs include a kanamycin resistance marker and, in 5' to 3' order, the CamV 35S promoter operably connected to a chloroplast division sequence, and an OCS terminator.

The CaMV 35S promoter is a constitutive promoter known to function in a wide variety of plants. Other promoters that are functional in the plant into which the construct will be introduced may be used to create genetic constructs to be used in the practice of the present invention. These may include other constitutive promoters, tissue-specific promoters, developmental stage-specific promoters, and inducible promoters. Promoters may also contain certain enhancer sequence elements that improve the efficiency of transcription.

The examples below describe the use of an expression vector that contains a kanamycin resistance gene as a selectable marker for selection of plants that have been transformed with the genetic construct. Numerous selectable markers, including antibiotic and herbicide resistance genes, are known in the art of plant molecular biology and may be used to construct expression vectors suitable for the practice of the present invention. Expression vectors may be engineered to include screenable markers, such as beta glucuronidase (GUS).

The genetic constructs employed in the examples below were engineered using the plasmid vectors pART7 and pART27 (Gleave, *Plant Mol. Biol.* 20:1203–1207, 1992). It is anticipated that other plasmid vectors or viral vectors, or other vectors that are known in the art of molecular biology, will be useful in the development of a construct that may be used to transform a plant to obtain expression of a plastid division sequence. We describe the creation of a genetic construct suitable for transformation using the Agrobacterium system. However, any transformation system for obtaining transgenic plants may be used. The construction of a vector and the adaptation of that vector to a particular transformation system are within the ability of one skilled in the art.

The present invention also contemplates a method for altering the number and size of plastids in a plant, relative to the wild type plant. The method comprises the steps of making a genetic construct comprising a plastid division sequence and a promoter, not be natively associated with the sequence, transforming the plant with the genetic construct, and growing the transgenic plant so created as to allow expression of the genetic construct. The genetic construct as a transgene in the plant will change plastid number in the plant.

In the examples below, changes in chloroplast numbers and size were examined in plants in which a plastid division sequence was expressed as a transgene in transgenic plants. It is expected that plastid division sequences are also involved in regulating the division of other plastids, including chromoplasts, amyloplasts, and elaioplasts. These plastids are of great agronomic importance because they synthesize carotenoids, starch, and oils, respectively. Manipulation of the expression of chloroplast division sequences to alter the number or size of plastids other than chloroplasts is within the scope and spirit of the present invention.

The nonlimiting examples that follow are intended to be purely illustrative.

EXAMPLES

Isolation and Characterization of a Chloroplast division gene from *Arabidopsis thaliana*

A homolog of the bacterial FtsZ genes was isolated from *Arabidopsis thaliana* as follows. The amino-acid sequence of *Escherichia coli* FtsZ was used as a probe in a homology search of the Expressed Sequence Tag database dbEST (Newman, T. et al. *Pl. Physiol.* 106:1241–1255, 1994). Complementary DNA from *Arabidopsis thaliana*, with no assigned matches in the database but exhibiting a small stretch of homology to *E. coli* FtsZ, was identified. A clone containing an Arabidopsis cDNA sequence homologous to the identified sequence in the plasmid pZL1 (Gibco-BRL) was obtained from the Arabidopsis Biological Resource Center (catalog number 105K17T7) and sequenced fully.

This Arabidopsis DNA sequence, designated cpFtsZ, is shown in SEQ ID NO:1. It contains an open reading frame (ORF) that encodes a putative protein of 433 amino acids (SEQ ID NO:2) with significant homology to FtsZ sequences from several prokaryotic species. The Arabidopsis FtsZ protein ($M_r$ 45,000) contains a glycine-rich "tubulin signature" motif which is conserved among FtsZ proteins and tubulins, and which is important for GTP binding (de Boer, et al. *Nature* 359:254–256, 1992). The ability to bind GTP suggests that cpftsz may have a function analogous to the cytoskeletal role of tubulin, which requires GTP-dependent polymerization for its activity. All but one of the amino acid residues that are identical in bacterial FtsZ proteins and tubulins ((Mukherjee, et al. *J. Bact.* 176:2754–2758, 1994) are conserved in the Arabidopsis cpFtsZ sequence.

Two lines of evidence suggest that Arabidopsis cpFtsZ protein is a nuclear-encoded protein that is localized in the stromal compartment of the chloroplast. The amino-terminal 45–55 residues of Arabidopsis cpFtsZ have properties typical of chloroplast transit peptides, which are characterized by a high proportion of hydroxylated amino acids, a paucity of acidic residues, and alanine as the second residue (Keegstra, et al., *A. Rev. Pl. Physiol., Pl. Molec. Biol.* 40:471–501, 1989).

Further evidence that the Arabidopsis cpFtsZ protein localizes in the chloroplast was provided through an in vitro chloroplast import experiment (Osteryoung et al. *Nature* 376:473–474, 1995). In that experiment, posttranslational import and processing of the full-length Arabidopsis cpFtsZ translation product was examined in isolated pea chloroplasts. The experiment demonstrated that the Arabidopsis cpFtsZ translation product is imported posttranslationally into chloroplasts where the putative transit peptide is cleaved, yielding a soluble protein that is protected from protease treatment unless the chloroplast membranes are disrupted with a detergent.

Identification of Additional FtsZ Homoloas in Arabidopsis

The existence of at least one additional FtsZ gene in Arabidopsis was indicated by the identification of a second EST in dbEST with a short stretch of homology to cpFtsZ. Because the sequence of this EST indicated that the cDNA had undergone rearrangement, a PCR fragment containing the region homologous to cpFtsZ was amplified and used to screen an Arabidopsis cDNA library. A nonrearranged cDNA clone was isolated and sequenced. This second cDNA sequence, designated AtFtsZ, is shown in SEQ ID NO:3. The deduced amino acid sequence (SEQ ID NO:4) exhibits approximately 50% identity to both cpFtsZ and to bacterial FtsZ proteins, and it contains all of the residues conserved among other FtsZ proteins. The deduced amino acid sequence is 56!k identical and 73% similar to Anabaena FtsZ, suggesting an endosymbiotic origin and chloroplast localization. However, in contrast to the cpFtsZ protein, the AtFtsZ in vitro translation product could not be imported into isolated chloroplasts; this may be because the AtFtsZ cDNA is not full-length, and is missing a region that encodes the transit peptide. That the cDNA does not contain the entire gene is suggested by the observation that the first ATG in the AtFtsZ cDNA occurs after a 38-amino acid ORF and is in a poor context to be an initiation codon (Lutke, et al. *EMBO J.* 6:43–48, 1987).

Hybridization studies performed under high stringency conditions using cpFtsZ cDNA to probe Southern and Northern blots of Arabidopsis sequences showed hybridization to a single band, indicating that cpFtsZ is likely encoded by a single gene in Arabidopsis.

Hybridization studies performed under high stringency conditions using the AtFtsZ cDNA as a probe revealed hybridization to two sequences distinct from that sequence to which cpFtsZ hybridized. This suggests that there may be a third Arabidopsis FtsZ sequence with significant homology to AtFtsZ.

Construction of Chimeric Antisense Genes

Figure 1:
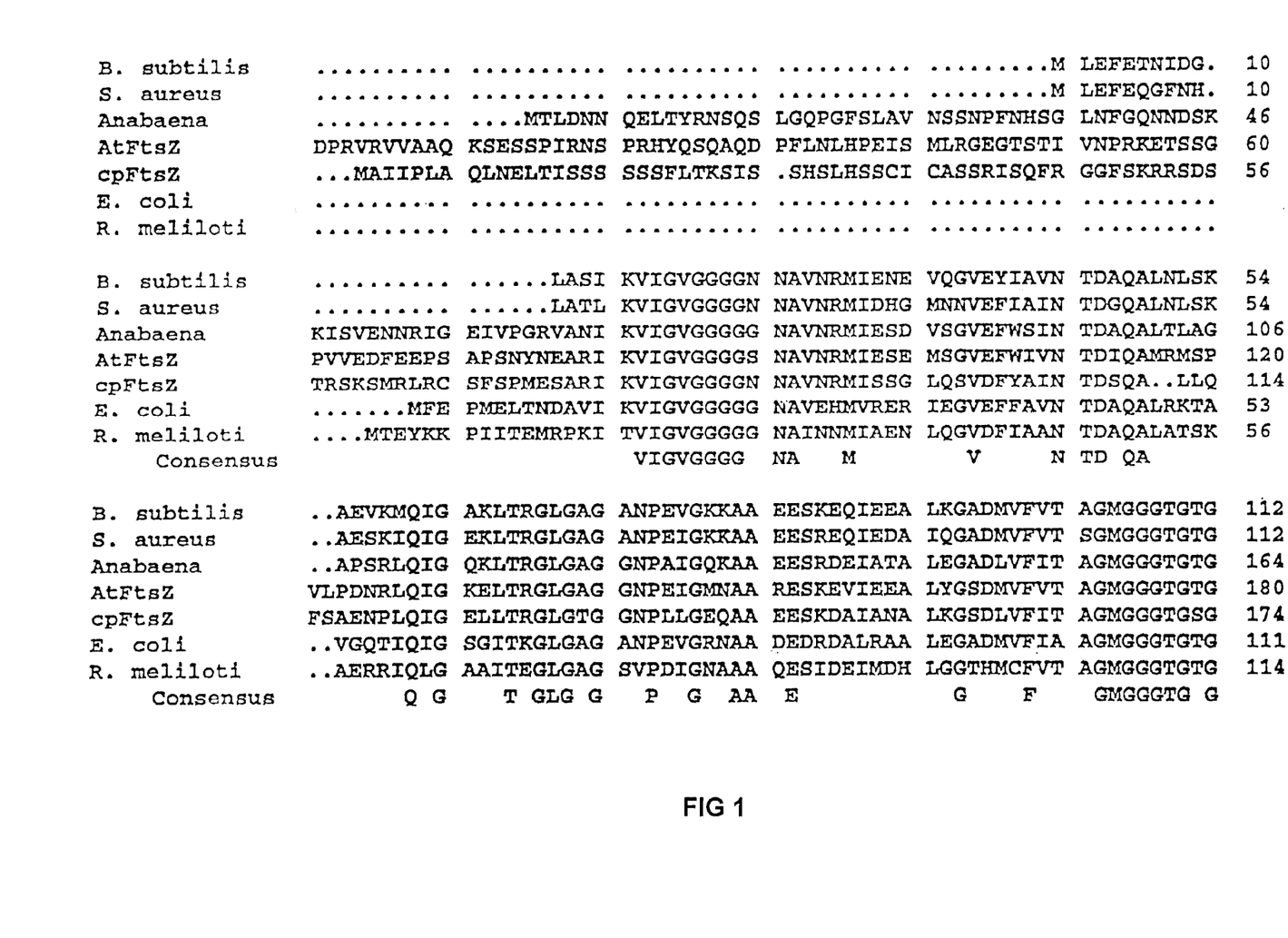
FIG. 1 is a sequence matching illustration of FtsZ genes.
Figure 2:
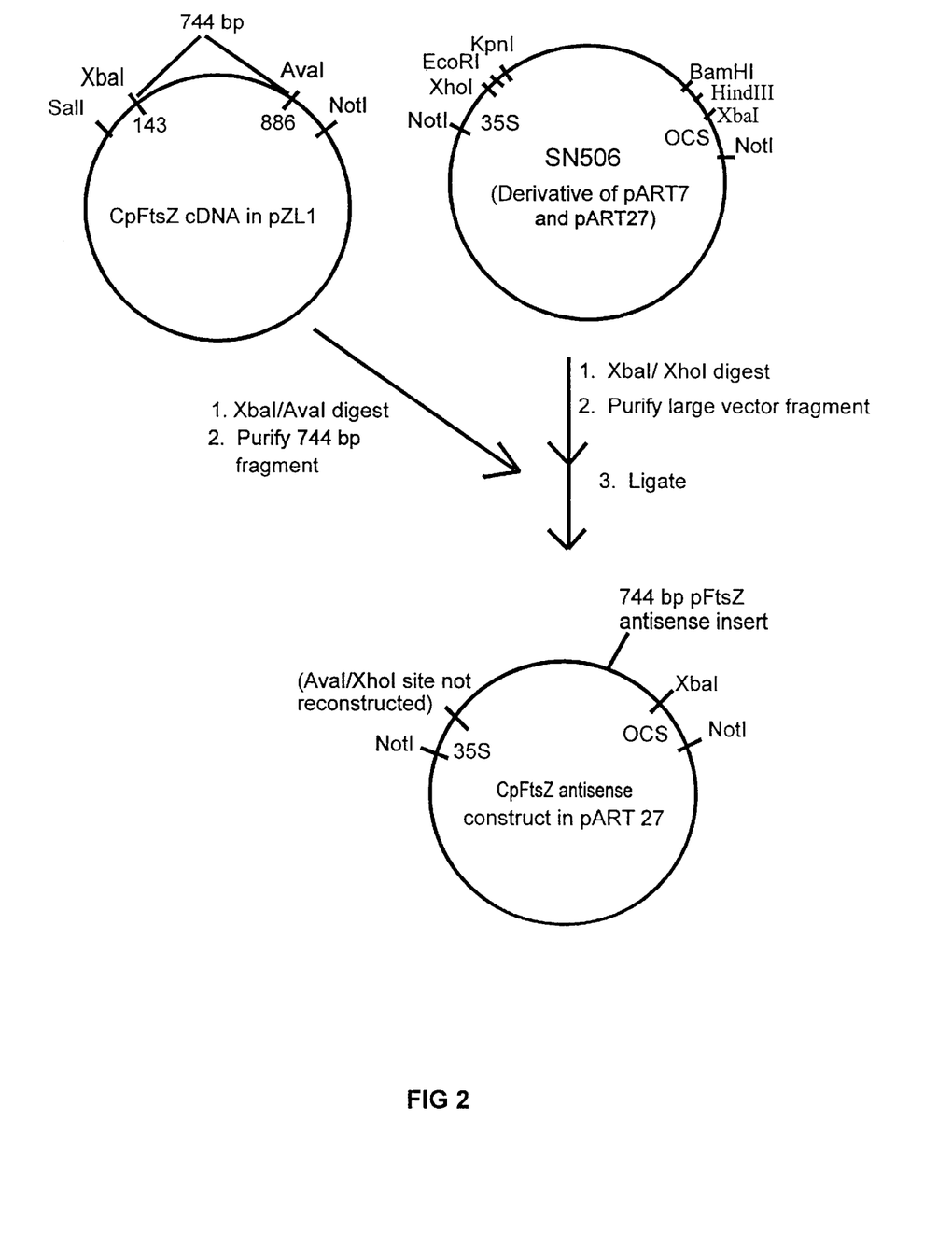
FIG. 2 is a schematic illustration of plasmid manipulations for the examples below.
Figure 3:
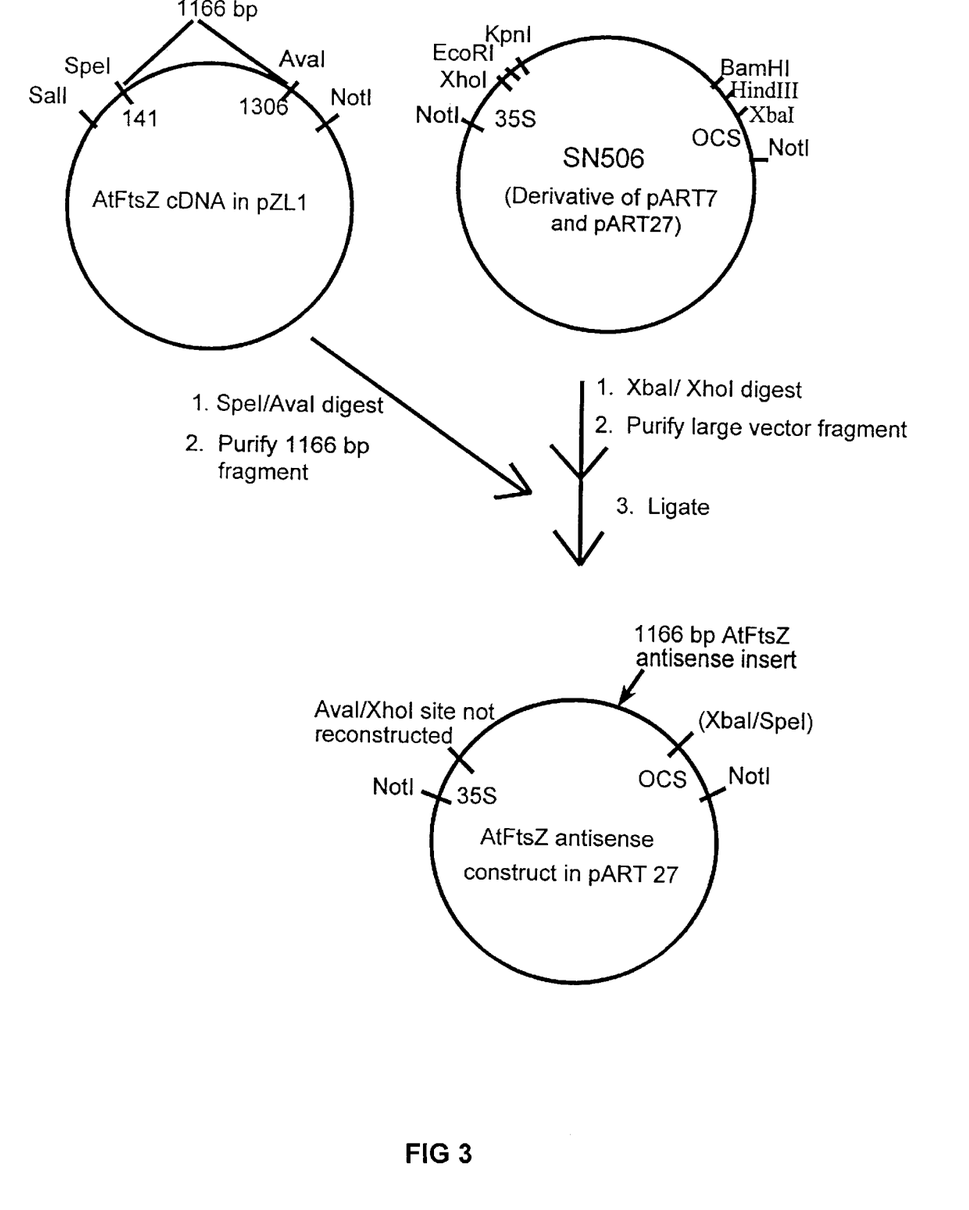
FIG. 3 is another schematic illustration of plasmid manipulations from the examples below.

To demonstrate that cpFtsZ and AtFtsZ function as plastid division genes, antisense genes were constructed to reduce expression of each gene and determine the effect on plastid number and size. The plant transformation vector chosen for these studies was pART27 (Gleave). Both antisense constructs were created using standard recombinant DNA techniques. The cpFtsZ antisense construct consisted of a 743 bp XbaI/AvaI restriction fragment that was ligated in the antisense orientation into a derivative of pART27 that contained compatible restrictions sites (FIG. 2). The AtFtsZ antisense construct consisted of a 1166 bp SpeI/AvaI restriction fragment that was ligated in the antisense orientation into the same pART27 derivative (FIG. 3). Following amplification of the ligation products in *E. coli*, miniprep DNA was purified by standard methods and subjected to several diagnostic restriction digests to verify proper insertion of the AtFtsZ or cpFtsZ fragments in the vector. Plasmid DNA isolated from E. coli transformants contained in 5' to 3' order, the cauliflower mosaic virus (CaMV) 35S promoter, the cpFtsZ or AtFtsZ gene fragment, and the OCS terminator.

Construction of Chimeric cDFtsZ Sense Gene

Figure 4:
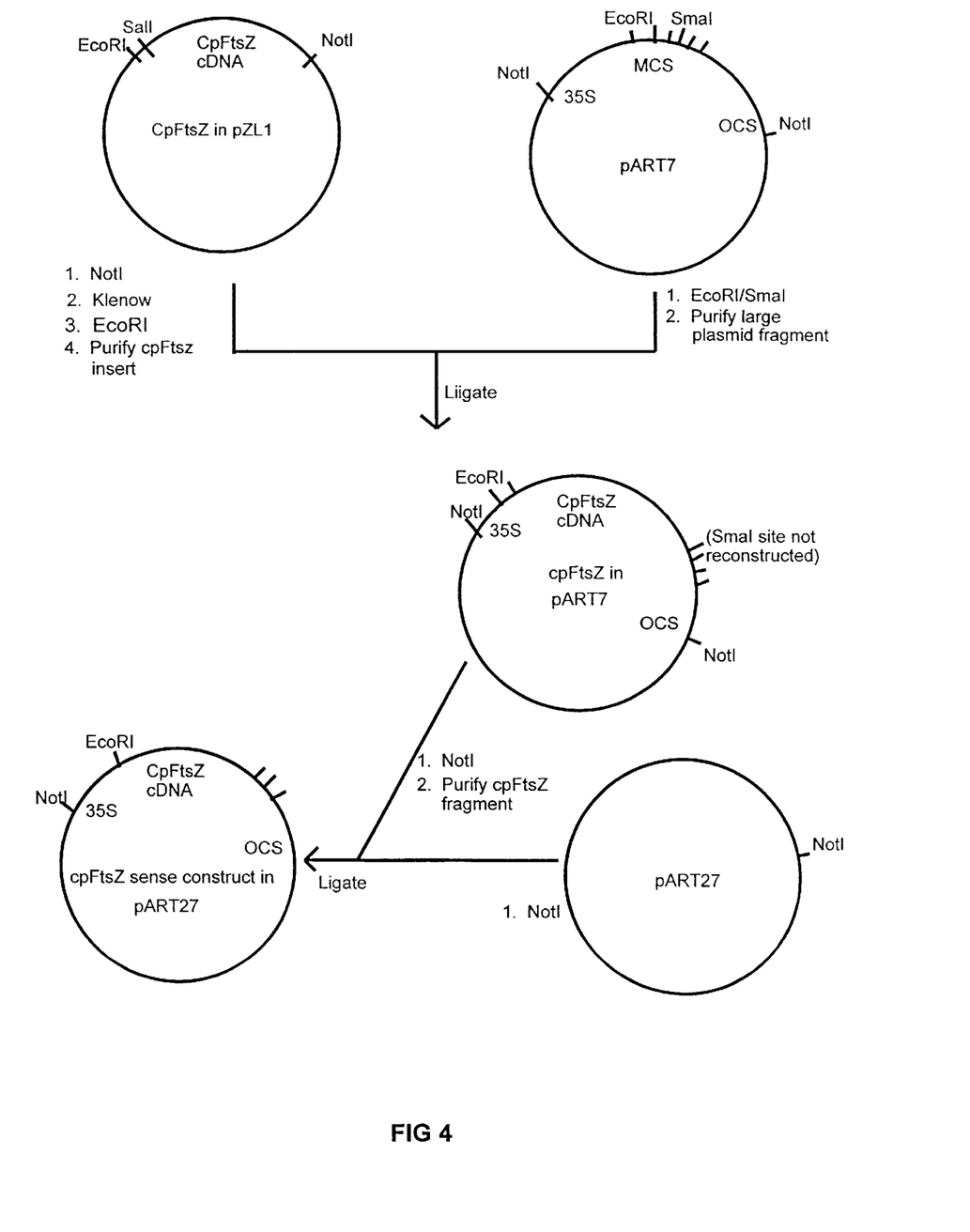
FIG. 4 is yet another schematic illustration of plasmid manipulations from the examples below.

A recombinant plasmid containing the cpFtsZ CDNA in the plasmid pZL1 (Gibco-BRL), obtained from the Arabidopsis Biological Resource Center (catalog number 105K17T7), was used for the construction of a cpFtsZ overexpression gene. The plasmid was linearized with NotI and the ends filled in with the Klenow fragment. A fragment containing the entire cpFtsZ cDNA was obtained by subsequent digestion of the plasmid with EcoRI and purified. This fragment was ligated directionally into pART7 that had been digested with SmaI and EcoRI. The resulting plasmid was digested with NotI. The fragment containing the chimeric cpFtsZ gene was purified and ligated into pART27 that had been digested with NotI. (See FIG. 4).

Transfer of the Chimeric Constructs Into Agrobacterium

Plasmid DNA was transferred to Agrobacterium strain GV3101 as follows: 1) 5 $\mu$l (approximately 1–2 $\mu$g) of a plasmid DNA preparation was added to previously frozen competent Agrobacterium cells that were thawed on ice; 2) the cells were frozen in liquid nitrogen, then thawed by incubating in a 37° C. water bath; 3) the cells were added to 1 ml of YEP (Yeast extract, peptone, sodium chloride) medium and incubated at 28° C. for 2–4 hours with gentle agitation; 4) the cells were transferred to a 1.5 ml centrifuge tube and pelleted by centrifugation for 30 seconds in a microcentrifuge (12,000 rpm); 5) the supernatant was decanted, and remaining pellet was resuspended in 100 $\mu$l of liquid YEP medium; 6) the cells were spread on YEP plates with the following antibiotics: rifampicin (50 $\mu$g/ml), spectinomycin (150 $\mu$g/ml), and gentamycin (25 $\mu$g/ml); 7) The colonies were incubated at 28° C. for 2 days.

To verify that no rearrangements had occurred following transfer of the plasmid to Agrobacterium, two isolated colonies for each construct were streaked onto separate plates containing YEP with rifampicin (50 $\mu$g/ml), spectinomycin (150 $\mu$g/ml), and gentamycin (25 $\mu$g/ml), and grown at 28° C. for 2 days. Five isolated colonies from each plate were transferred to separate culture tubes, containing 3 ml LB liquid media and 100 $\mu$g/ml spectinomycin, and grown for two days in a 30° C. shaking incubator. Small scale DNA preparations (minipreps) of recombinant plasmids were made by standard methods. Each of the five DNA samples were suspended in 5 $\mu$l and pooled. The DNA was subject to several diagnostic restriction digests, and the sizes of the resulting fragments were determined by agarose gel electrophoresis. Digestion of plasmid DNA isolated from Agrobacterium gave fragments of the same sizes as those obtained from similarly digested plasmid DNA isolated from *E. coli*. The results indicated that no rearrangement of the inserted DNA occurred.

Transformation of *Arabidopsis thaliana*

A single colony of Agrobacterium transformed with the appropriate construct was transferred to a flask containing 25 ml YEP with rifampicin (50 μg/ml), spectinomycin (150 μg/ml), and gentamycin (25 μg/ml). After a one day incubation in a 30° C. shaking incubator, the 25 ml culture was transferred to 1 liter of YEP medium containing the same antibiotics as above. The Agrobacterium cells were incubated at 30° C. overnight in a shaking incubator. The Agrobacterium culture was pelleted by centrifugation in a centrifuge at 6000 rpms for 15 minutes. The cell pellet was resuspended in 4 liters of infiltration medium (8.8 g Murashige-Skoog salts (Gibco-BRL), 4 ml Gamborg's 1×B5 vitamins (Gibco-BRL), 2 g MES, pH 5.7, 18 μl benzylaminopurine, 800 μl Silwett L-77). Five pots, each with five 6 week-old *Arabidopsis thaliana* plants, were placed into a sealed glass vacuum with the infiltration medium and held at 15 inches Hg for 5 minutes. Plants were then placed into a Percival environmental growth chamber at 16 hour light at 20° C., and 8 hour night at 15° C., 70% humidity and 100–150 μmol m$^{-2}$ s$^{-1}$ intensity. Seeds were harvested at maturity.

Identification of Transformed T1 Generation Seedlings

Seeds were sterilized and transferred to MS plates (Murashige-salts 4.3 g/L, sucrose 20 g/L, phytagar 7 g/L, pH 5.8) containing 100 μg/ml kanamycin. The plates were placed into a 4° C. refrigerator for 2 days to vernalize the seeds and then placed into a 20° C. growth chamber (16 hour light at 20° C. and 8 hour dark at 15° C.). Transformed plants displaying kanamycin resistance were evidenced by seedlings that grew first leaves and long branching roots. Kanamycin-sensitive seedlings germinated bleached cotyledons and nonbranching roots. Dark green kanamycin-resistant transformants were transferred to soil with vermiculite and 1×Hoaglands and grown to maturity for collection of T2 seed.

Examination of Altered cpFtsZ or AtFtsZ Expression on Chloroplast Number and Size.

To determine whether altered cpFtsZ or AtFtsZ expression affects plastid division, transgenic lines were examined for changes in plastid number and size using methods described by Pyke and Leech (*Plant Physiol.* 96:1193–1195, 1991). Small pieces of cotyledon or leaf tissue from T1 or T2 transformants were fixed in 3.5% glutaraldehyde for 1 hour, then transferred to 0.1% Na$_2$EDTA pH 8.0 and incubated for 3–5 hr at 55° C. Mesophyll cells were teased apart and examined under an Olympus BH-2 microscope using Nomarski interference contrast optics to allow visualization of chloroplasts.

Alterations in Chloroplast Number and Size in Transformants.

Transformants containing introduced cpFtsZ or AtFtsZ sequences were found to exhibit unique phenotypes characterized by reduced numbers of chloroplasts that are much larger than wild type chloroplasts (Table 1). These results confirm that these sequences play an important role in chloroplast division, and indicate that chloroplast numbers can be manipulated in transgenic plants.

Approximately 60% of the 98 AtFtsZ antisense transformants examined had reduced numbers of enlarged chloroplasts relative to wild types. Roughly half of the transformants had only about 1–4 greatly enlarged chloroplasts, and approximately 10% had from about 5–20 enlarged chloroplasts (Table 1). Approximately 40% of the transformants had wild type numbers of chloroplasts (from 80–100) of normal size. of the twenty-five transformants having the construct containing cpFtsZ in the sense orientation, seven had mesophyll cells that had greatly reduced numbers of very large chloroplasts. Seven of the cpFtsZ sense mutants had the wild type phenotype, four had an intermediate phenotype, and four had a mixed phenotype. Three transformants had increased numbers of plastids that were smaller than in wild type (Table 1).

Twenty-six transformants were obtained that contained the construct with cpFtsZ in the antisense orientation. Of these plants, thirteen exhibited the wild type phenotype, four had severely reduced numbers of very large chloroplast, one had an intermediate phenotype, thirteen had a wild type phenotype, and one had mesophyll cells having chloroplasts of a variety of sizes (Table 1).

Taken together, these results indicate that either decreased or increased numbers of chloroplasts can be obtained in transgenic plants by manipulation of cpFtsZ or AtFtsZ expression levels.

TABLE 1

Phenotypes of Arabidopsis AtFtsZ and cpFtsZ transgenic plants

| Gene | Direction | Severe (1–4 plastids) Very Large | Intermediate (5–20 plastids) Larger than WT | Wild Type (80–100 plastids) | Mixed* | Plastids Smaller Than Wild Type | Total |
|---|---|---|---|---|---|---|---|
| AtFtsZ | Antisense | 48 | 10 | 39 | 1 | — | 98 |
| cpFtsz | Antisense | 4 | 1 | 13 | 8 | — | 26 |
| cpFtsZ | Sense | 7 | 4 | 7 | 4 | 3 | 25 |

The data provide confirmation that cpFtsZ and AtFtsZ are chloroplast division genes.
*Different plastid numbers in different cells from the same plant.

Identification of FtsZ Sequences in Other Plant Species.

To determine whether other plant species contain DNA sequences with homology to the Arabidopsis cpFtsZ or AtFtsZ sequences, Southern hybridization experiments were performed as follows. Genomic DNA was isolated from numerous plant species according to standard methods known to the art. The DNA was digested with EcoRI and separated electrophoretically on an agarose gel. The DNA fragments were transferred to a nitrocellulose membrane by Southern blotting. The cpFtsZ cDNA was isolated from pZL1 by digestion with Not I and Sal I, radiolabeled with $^{32}$P-dATP, and hybridized to the blot at 42° C. in aqueous buffer as described (Ausabel et al., Current Protocols in Molecular Biology, John Wiley & Sons, 1994). The blot was washed at moderate stringency (0.2×SSC, 45° C.) and exposed to x-ray film. Two or more bands hybridized to the cpFtsZ probe in every species represented on the blot. These results indicate that FtsZ homologs exist in other plant species and are encoded by a small gene family.

The results of this hybridization experiment (FIG. X) provide evidence that numerous diverse plant species contain sequences having homology to the plastid division genes of Arabidopsis.

I claim:

1. A transgenic plant comprising in its genome a genetic construct comprising a sense or antisense Arabidopsis plastid division FtsZ protein coding sequence and a promoter, not natively associated with the FtsZ protein coding sequence, which promotes expression of the Arabidopsis FtsZ protein coding sequence in the plant, wherein expression of the sequence in the plant causes alterations in the number and size of plastids in plant cells of the plant as compared to nontransgenic plants of the species.

2. A transgenic plant comprising in its genome a genetic construct comprising a sense or antisense plastid division sequence and a promoter, not natively associated with the sequence, which promotes expression of the sequence in the plant, wherein expression of the sequence in the plant causes alterations in the number and size of plastids in plant cells of the plant as compared to nontransgenic plants of the species, wherein the sequence comprises a sequence selected from the group consisting of SEQ ID NO:1 and SEQ ID NO:3.

3. The plant of claim 1, wherein the construct comprises in 5' to 3' order a CaMV 35S promoter, an FtsZ plant plastid division sequence selected from the group consisting of SEQ ID NO:1 and SEQ ID NO:3, and an OCS terminator.

4. The plant of claim 1, wherein the plastids are chloroplasts.

5. A DNA sequence comprising the sequence of SEQ ID NO:1.

6. A DNA sequence comprising the sequence of SEQ ID NO:2.

7. Seed of the plant of claim 1.

8. A plant comprising in its genome a transgene comprising a sense or antisense Arabidopsis FtsZ gene which causes the plant to have an altered number of plastids as compared to plants of the same species without the transgene.

9. Seeds of the plant of claim 8.

10. A plant as claimed in claim 8 wherein the coding sequence of the FtsZ gene is selected from the group consisting of cpFtsZ and AtFtsZ.

11. A plant seed comprising in its genome a genetic construct comprising a sense or antisense Arabidopsis plastid division FtsZ protein coding sequence and a promoter, not natively associated with the FtsZ protein coding sequence, which promotes expression of the Arabidopsis FtsZ protein coding sequence in a plant, wherein expression of the sequence in the plant causes alterations in the number and size of plastids in plant cells of the plant.

12. A genetic construct comprising an Arabideopis FtsZ plastid division protein coding sequence in either a sense or antisense orientation and a promoter that promotes expression of the sequence in plants, the promoter not being natively associated with the plastid division sequence.

13. A genetic construct comprising a plastid division sequence in either a sense or antisense orientation and a promoter that promotes expression of the sequence in plants, the promoter not being natively associated with the plastid division sequence, wherein the plastid division sequence is chosen from the group consisting of SEQ ID NO:1 and SEQ ID NO:3.

14. The genetic construct of claim 12, wherein the promoter is the CaMV 35S promoter.

15. The genetic construct of claim 12, additionally comprising a kanamycin resistance marker.

16. A method for altering the number and size of plastids in plant cells of a plant comprising the steps of constructing a genetic construct comprising an Arabidopsis plastid division FtsZ protein coding sequence in either a sense or antisense orientation and a promoter, not natively associated with the FtsZ protein coding sequence, which promotes expression of the Arabidopsis FtsZ protein coding sequence in plants, introducing the genetic construct into a plant, selecting a plant that has received a copy of the genetic construct, and growing the plant under conditions that allow expression of the gene.

17. A DNA sequence isolated from its native genome comprising an Arabidopsis FtsZ gene.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1425 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 25..1326

(xi) SEQUENCE DESCRIPTION: SEQ ID NO:1:

```
CCACGCGTCC GGAGGAAGTA AACA ATG GCG ATA ATT CCG TTA GCA CAG CTT                51
                          Met Ala Ile Ile Pro Leu Ala Gln Leu
                            1               5

AAT GAG CTA ACG ATT TCT TCA TCT TCT TCT TCG TTT CTT ACC AAA TCG                99
Asn Glu Leu Thr Ile Ser Ser Ser Ser Ser Ser Phe Leu Thr Lys Ser
 10              15                  20                  25

ATA TCT TCT CAT TCG TTG CAT AGT AGC TGC ATT TGC GCA AGT TCT AGA               147
Ile Ser Ser His Ser Leu His Ser Ser Cys Ile Cys Ala Ser Ser Arg
                 30                  35                  40

ATC AGT CAA TTC CGT GGC GGC TTC TCT AAA CGA AGA AGC GAT TCA ACA               195
Ile Ser Gln Phe Arg Gly Gly Phe Ser Lys Arg Arg Ser Asp Ser Thr
             45                  50                  55

AGG TCT AAG TCG ATG CGA TTG AGG TGT TCC TTC TCT CCG ATG GAA TCT               243
Arg Ser Lys Ser Met Arg Leu Arg Cys Ser Phe Ser Pro Met Glu Ser
         60                  65                  70

GCG AGA ATT AAG GTG ATT GGT GTC GGT GGT GGT GGT AAC AAT GCC GTT               291
Ala Arg Ile Lys Val Ile Gly Val Gly Gly Gly Gly Asn Asn Ala Val
     75                  80                  85

AAC CGG ATG ATT TCA AGC GGT TTA CAG AGT GTT GAT TTC TAT GCG ATA               339
Asn Arg Met Ile Ser Ser Gly Leu Gln Ser Val Asp Phe Tyr Ala Ile
 90                  95                 100                 105

AAC ACG GAT TCG CAA GCT CTG TTA CAG TTT TCT GCT GAG AAC CCA CTT               387
Asn Thr Asp Ser Gln Ala Leu Leu Gln Phe Ser Ala Glu Asn Pro Leu
                110                 115                 120

CAA ATT GGA GAA CTT TTA ACT CGT GGG CTT GGC ACT GGT GGA AAC CCG               435
Gln Ile Gly Glu Leu Leu Thr Arg Gly Leu Gly Thr Gly Gly Asn Pro
            125                 130                 135

CTT CTT GGA GAA CAA GCT GCA GAA GAA TCA AAA GAT GCA ATT GCT AAT               483
Leu Leu Gly Glu Gln Ala Ala Glu Glu Ser Lys Asp Ala Ile Ala Asn
        140                 145                 150

GCT CTT AAA GGA TCA GAC CTT GTT TTC ATA ACT GCT GGT ATG GGT GGT               531
Ala Leu Lys Gly Ser Asp Leu Val Phe Ile Thr Ala Gly Met Gly Gly
    155                 160                 165

GGA ACA GGG TCT GGT GCT GCA CCT GTG GTA GCT CAG ATT TCG AAG GAT               579
Gly Thr Gly Ser Gly Ala Ala Pro Val Val Ala Gln Ile Ser Lys Asp
170                 175                 180                 185

GCT GGT TAT TTG ACT GTT GGT GTT GTT ACC TAT CCG TTT AGC TTT GAA               627
Ala Gly Tyr Leu Thr Val Gly Val Val Thr Tyr Pro Phe Ser Phe Glu
```

```
                190              195             200
GGA CGT AAA AGA TCT TTG CAG GCA CTG GAA GCT ATT GAA AAG CTC CAA        675
Gly Arg Lys Arg Ser Leu Gln Ala Leu Glu Ala Ile Glu Lys Leu Gln
            205             210             215

AAG AAT GTT GAT ACC CTT ATC GTG ATT CCA AAT GAT CGT CTG CTA GAT        723
Lys Asn Val Asp Thr Leu Ile Val Ile Pro Asn Asp Arg Leu Leu Asp
            220             225             230

ATT GCT GAT GAA CAG ACG CCA CTT CAG GAC GCG TTT CTT CTT GCA GAT        771
Ile Ala Asp Glu Gln Thr Pro Leu Gln Asp Ala Phe Leu Leu Ala Asp
            235             240             245

GAT GTT TTA CGC CAA GGA GTA CAA GGA ATC TCA GAT ATT ATT ACT ATA        819
Asp Val Leu Arg Gln Gly Val Gln Gly Ile Ser Asp Ile Ile Thr Ile
250             255             260             265

CCT GGA CTA GTC AAT GTG GAT TTT GCA GAT GTG AAG GCA GTC ATG AAA        867
Pro Gly Leu Val Asn Val Asp Phe Ala Asp Val Lys Ala Val Met Lys
                270             275             280

GAT TCT GGA ACT GCA ATG CTC GGG GTA GGT GTT TCT TCC AGC AAA AAC        915
Asp Ser Gly Thr Ala Met Leu Gly Val Gly Val Ser Ser Ser Lys Asn
                285             290             295

CGG GCA GAA GAA GCA GCT GAA CAA GCA ACT TTG GCT CCA TTG ATC GGA        963
Arg Ala Glu Glu Ala Ala Glu Gln Ala Thr Leu Ala Pro Leu Ile Gly
            300             305             310

TCA TCC ATA CAA TCA GCT ACT GGT GTC GTC TAC AAC ATC ACT GGT GGA       1011
Ser Ser Ile Gln Ser Ala Thr Gly Val Val Tyr Asn Ile Thr Gly Gly
            315             320             325

AAA GAC ATA ACT TTG CAG GAA GTG AAC CGA GTA TCA CAG GTC GTG ACA       1059
Lys Asp Ile Thr Leu Gln Glu Val Asn Arg Val Ser Gln Val Val Thr
330             335             340             345

AGT TTG GCA GAC CCA TCG GCC AAC ATC ATA TTT GGA GCT GTT GTG GAT       1107
Ser Leu Ala Asp Pro Ser Ala Asn Ile Ile Phe Gly Ala Val Val Asp
                350             355             360

GAT CGC TAC ACC GGA GAG ATT CAT GTA ACG ATA ATC GCC ACA GGC TTC       1155
Asp Arg Tyr Thr Gly Glu Ile His Val Thr Ile Ile Ala Thr Gly Phe
                365             370             375

TCT CAG TCA TTC CAG AAG ACA CTT CTG ACT GAT CCA AGA GCA GCT AAA       1203
Ser Gln Ser Phe Gln Lys Thr Leu Leu Thr Asp Pro Arg Ala Ala Lys
            380             385             390

CTC CTT GAC AAA ATG GGA TCA TCA GGT CAA CAA GAG AAC AAA GGA ATG       1251
Leu Leu Asp Lys Met Gly Ser Ser Gly Gln Gln Glu Asn Lys Gly Met
395             400             405

TCT CTG CCT CAC CAG AAG CAG TCT CCA TCA ACT ATC TCT ACC AAA TCG       1299
Ser Leu Pro His Gln Lys Gln Ser Pro Ser Thr Ile Ser Thr Lys Ser
410             415             420             425

TCT TCT CCC CGT AGA CTT TTC TTC TAG TTTTCTTTTT TTCCTTTTCG            1346
Ser Ser Pro Arg Arg Leu Phe Phe *
                430

GTTTCAAGCA TCAAAAATGT AACGATCTTC AGGCTCAAAT ATCAATTACA TTTGATTTTC    1406

CTCCAAAAAA AAAAAAAA                                                  1425

(2) INFORMATION FOR SEQ ID NO:2:

(i) SEQUENCE CHARACTERISTICS:
        (A) LENGTH:   433 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ile Ile Pro Leu Ala Gln Leu Asn Glu Leu Thr Ile Ser Ser
 1               5                  10                  15
```

-continued

```
Ser Ser Ser Ser Phe Leu Thr Lys Ser Ile Ser Ser His Ser Leu His
            20                  25                  30

Ser Ser Cys Ile Cys Ala Ser Ser Arg Ile Ser Gln Phe Arg Gly Gly
            35                  40                  45

Phe Ser Lys Arg Arg Ser Asp Ser Thr Arg Ser Lys Ser Met Arg Leu
            50                  55                  60

Arg Cys Ser Phe Ser Pro Met Glu Ser Ala Arg Ile Lys Val Ile Gly
 65                      70                  75                  80

Val Gly Gly Gly Asn Asn Ala Val Asn Arg Met Ile Ser Ser Gly
                85                  90                  95

Leu Gln Ser Val Asp Phe Tyr Ala Ile Asn Thr Asp Ser Gln Ala Leu
                100                 105                 110

Leu Gln Phe Ser Ala Glu Asn Pro Leu Gln Ile Gly Glu Leu Leu Thr
                115                 120                 125

Arg Gly Leu Gly Thr Gly Gly Asn Pro Leu Leu Gly Glu Gln Ala Ala
    130                 135                 140

Glu Glu Ser Lys Asp Ala Ile Ala Asn Ala Leu Lys Gly Ser Asp Leu
145                 150                 155                 160

Val Phe Ile Thr Ala Gly Met Gly Gly Thr Gly Ser Gly Ala Ala
                165                 170                 175

Pro Val Val Ala Gln Ile Ser Lys Asp Ala Gly Tyr Leu Thr Val Gly
                180                 185                 190

Val Val Thr Tyr Pro Phe Ser Phe Glu Gly Arg Lys Arg Ser Leu Gln
                195                 200                 205

Ala Leu Glu Ala Ile Glu Lys Leu Gln Lys Asn Val Asp Thr Leu Ile
                210                 215                 220

Val Ile Pro Asn Asp Arg Leu Leu Asp Ile Ala Asp Glu Gln Thr Pro
225                 230                 235                 240

Leu Gln Asp Ala Phe Leu Leu Ala Asp Asp Val Leu Arg Gln Gly Val
                245                 250                 255

Gln Gly Ile Ser Asp Ile Ile Thr Ile Pro Gly Leu Val Asn Val Asp
                260                 265                 270

Phe Ala Asp Val Lys Ala Val Met Lys Asp Ser Gly Thr Ala Met Leu
                275                 280                 285

Gly Val Gly Val Ser Ser Lys Asn Arg Ala Glu Ala Ala Glu
290                 295                 300

Gln Ala Thr Leu Ala Pro Leu Ile Gly Ser Ser Ile Gln Ser Ala Thr
305                 310                 315                 320

Gly Val Val Tyr Asn Ile Thr Gly Gly Lys Asp Ile Thr Leu Gln Glu
                325                 330                 335

Val Asn Arg Val Ser Gln Val Val Thr Ser Leu Ala Asp Pro Ser Ala
                340                 345                 350

Asn Ile Ile Phe Gly Ala Val Val Asp Asp Arg Tyr Thr Gly Glu Ile
                355                 360                 365

His Val Thr Ile Ile Ala Thr Gly Phe Ser Gln Ser Phe Gln Lys Thr
    370                 375                 380

Leu Leu Thr Asp Pro Arg Ala Ala Lys Leu Leu Asp Lys Met Gly Ser
385                 390                 395                 400

Ser Gly Gln Gln Glu Asn Lys Gly Met Ser Leu Pro His Gln Lys Gln
                405                 410                 415

Ser Pro Ser Thr Ile Ser Thr Lys Ser Ser Ser Pro Arg Arg Leu Phe
                420                 425                 430

Phe
```

(2) INFORMATION FOR SEQ ID NO:3:

(i) SEQUENCE CHARACTERISTICS:
        (A) LENGTH: 1628 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 3..1316

(xi) SEQUENCE DESCRIPTION: SEQ ID NO:3:

```
TC GAC CCA CGC GTC CGT GTT GTT GCC GCT CAG AAA TCT GAA TCT TCT        47
   Asp Pro Arg Val Arg Val Val Ala Ala Gln Lys Ser Glu Ser Ser
   435                 440                 445

CCA ATC AGA AAC TCT CCA CGG CAT TAC CAA AGC CAA GCT CAA GAT CCT       95
Pro Ile Arg Asn Ser Pro Arg His Tyr Gln Ser Gln Ala Gln Asp Pro
450                 455                 460                 465

TTC TTG AAC CTT CAC CCG GAA ATA TCT ATG CTT AGA GGT GAA GGG ACT      143
Phe Leu Asn Leu His Pro Glu Ile Ser Met Leu Arg Gly Glu Gly Thr
                470                 475                 480

AGT ACA ATA GTC AAT CCA AGA AAG GAA ACG TCT TCT GGA CCT GTT GTC      191
Ser Thr Ile Val Asn Pro Arg Lys Glu Thr Ser Ser Gly Pro Val Val
            485                 490                 495

GAG GAT TTT GAA GAG CCA TCT GCT CCG AGT AAC TAC AAT GAG GCG AGG      239
Glu Asp Phe Glu Glu Pro Ser Ala Pro Ser Asn Tyr Asn Glu Ala Arg
        500                 505                 510

ATT AAG GTT ATT GGT GTG GGA GGT GGT GGA TCA AAT GCT GTG AAT CGT      287
Ile Lys Val Ile Gly Val Gly Gly Gly Gly Ser Asn Ala Val Asn Arg
    515                 520                 525

ATG ATA GAG AGT GAA ATG TCA GGT GTG GAG TTC TGG ATT GTC AAC ACT      335
Met Ile Glu Ser Glu Met Ser Gly Val Glu Phe Trp Ile Val Asn Thr
530                 535                 540                 545

GAT ATC CAG GCT ATG AGA ATG TCT CCT GTT TTG CCT GAT AAT AGG TTA      383
Asp Ile Gln Ala Met Arg Met Ser Pro Val Leu Pro Asp Asn Arg Leu
                550                 555                 560

CAA ATT GGT AAG GAG TTG ACT AGG GGT TTA GGT GCT GGA GGA AAT CCA      431
Gln Ile Gly Lys Glu Leu Thr Arg Gly Leu Gly Ala Gly Gly Asn Pro
            565                 570                 575

GAA ATC GGT ATG AAT GCT GCT AGA GAG AGC AAA GAA GTT ATT GAA GAA      479
Glu Ile Gly Met Asn Ala Ala Arg Glu Ser Lys Glu Val Ile Glu Glu
        580                 585                 590

GCT CTT TAT GGC TCA GAT ATG GTC TTT GTC ACA GCT GGA ATG GGC GGT      527
Ala Leu Tyr Gly Ser Asp Met Val Phe Val Thr Ala Gly Met Gly Gly
    595                 600                 605

GGA ACT GGC ACT GGT GCA GCC CCT GTA ATT GCA GGA ATT GCC AAG GCG      575
Gly Thr Gly Thr Gly Ala Ala Pro Val Ile Ala Gly Ile Ala Lys Ala
610                 615                 620                 625

ATG GGT ATA TTG ACA GTT GGT ATT GCC ACA ACG CCT TTC TCG TTT GAG      623
Met Gly Ile Leu Thr Val Gly Ile Ala Thr Thr Pro Phe Ser Phe Glu
                630                 635                 640

GGT CGA AGA AGA ACT GTT CAG GCT CAA GAA GGG CTT GCA TCT CTC AGA      671
Gly Arg Arg Arg Thr Val Gln Ala Gln Glu Gly Leu Ala Ser Leu Arg
            645                 650                 655

GAC AAT GTT GAC ACT CTC ATC GTC ATT CCA AAT GAC AAG TTG CTT ACA      719
Asp Asn Val Asp Thr Leu Ile Val Ile Pro Asn Asp Lys Leu Leu Thr
        660                 665                 670

GCT GTC TCT CAG TCT ACT CCG GTA ACA GAA GCA TTT AAT CTA GCT GAT      767
Ala Val Ser Gln Ser Thr Pro Val Thr Glu Ala Phe Asn Leu Ala Asp
```

```
           675                 680                 685
GAT ATA CTC CGT CAG GGG GTT CGT GGG ATA TCT GAT ATC ATT ACG ATT      815
Asp Ile Leu Arg Gln Gly Val Arg Gly Ile Ser Asp Ile Ile Thr Ile
690                 695                 700                 705

CCT GGT TTG GTG AAT GTG GAT TTT GCT GAT GTG AGA GCT ATA ATG GCA      863
Pro Gly Leu Val Asn Val Asp Phe Ala Asp Val Arg Ala Ile Met Ala
                710                 715                 720

AAT GCG GGG TCT TCA TTG ATG GGA ATA GGA ACT GCA ACA GGA AAG AGT      911
Asn Ala Gly Ser Ser Leu Met Gly Ile Gly Thr Ala Thr Gly Lys Ser
            725                 730                 735

CGG GCA AGA GAT GCT GCG CTA AAT GCA ATC CAA TCC CCT TTG TTA GAT      959
Arg Ala Arg Asp Ala Ala Leu Asn Ala Ile Gln Ser Pro Leu Leu Asp
        740                 745                 750

ATT GGG ATT GAG AGA GCC ACT GGA ATT GTT TGG AAC ATT ACT GGC GGA     1007
Ile Gly Ile Glu Arg Ala Thr Gly Ile Val Trp Asn Ile Thr Gly Gly
    755                 760                 765

AGT GAC TTG ACA TTG TTT GAG GTA AAT GCT GCT GCG GAA GTA ATA TAT     1055
Ser Asp Leu Thr Leu Phe Glu Val Asn Ala Ala Ala Glu Val Ile Tyr
770                 775                 780                 785

GAT CTT GTC GAT CCA ACT GCC AAT CTT ATA TTC GGT GCT GTT GTA GAT     1103
Asp Leu Val Asp Pro Thr Ala Asn Leu Ile Phe Gly Ala Val Val Asp
                790                 795                 800

CCA GCC CTC AGC GGT CAA GTA AGC ATA ACC CTG ATA GCT ACG GGT TTC     1151
Pro Ala Leu Ser Gly Gln Val Ser Ile Thr Leu Ile Ala Thr Gly Phe
            805                 810                 815

AAA CGA CAA GAA GAG GGA GAA GGA CGA ACA GTT CAG ATG GTA CAA GCA     1199
Lys Arg Gln Glu Glu Gly Glu Gly Arg Thr Val Gln Met Val Gln Ala
        820                 825                 830

GAT GCT GCG TCA GTT GGA GCT ACA AGA AGA CCC TCT TCT TCC TTT AGA     1247
Asp Ala Ala Ser Val Gly Ala Thr Arg Arg Pro Ser Ser Ser Phe Arg
    835                 840                 845

GAA AGC GGT TCA GTG GAG ATC CCA GAG TTC TTG AAG AAG AAA GGC AGC     1295
Glu Ser Gly Ser Val Glu Ile Pro Glu Phe Leu Lys Lys Lys Gly Ser
850                 855                 860                 865

TCT CGT TAT CCC CGA GTC TAA AGCCCAATCT AATCACTACC CTGCACACTG        1346
Ser Arg Tyr Pro Arg Val  *
                870

CAGCAATAAC AAACGTGTGT GTACTGGTAG TCTGGTACTG CCTTCTGGGA TACAGCAAGA   1406

TGTGTTGATG TATGATCAAG AATCTGTGTG GGTGTGTATA TGTTCTGTCA CTGCCTCTGG   1466

TCGTGTTCTT GAATAGGTTG TTTTAGAAAT CGGAGTTTCT CTCTATGTCA CTTCCAAAAC   1526

AAAAAAGGAG AAGAAGAATC ACACTTCTCG AACCATAAAC ATACTTATAA GATTATGAGA   1586

GTTTTAGCAG AAATTATTGT CAAAAAAAAA AAAAAAAAA AA                      1628

(2) INFORMATION FOR SEQ ID NO:4:

(i) SEQUENCE CHARACTERISTICS:
        (A) LENGTH:  437 amino acids
        (B) TYPE: amino acid
        (D) TOPOLOGY: linear (ii) MOLECULE TYPE: protein (xi) SEQUENCE DESCRIPTION: SEQ ID NO:4:

Asp Pro Arg Val Arg Val Val Ala Ala Gln Lys Ser Glu Ser Ser Pro
1               5                   10                  15

Ile Arg Asn Ser Pro Arg His Tyr Gln Ser Gln Ala Gln Asp Pro Phe
            20                  25                  30

Leu Asn Leu His Pro Glu Ile Ser Met Leu Arg Gly Glu Gly Thr Ser
        35                  40                  45
```

```
Thr Ile Val Asn Pro Arg Lys Glu Thr Ser Ser Gly Pro Val Val Glu
     50                  55                  60

Asp Phe Glu Glu Pro Ser Ala Pro Ser Asn Tyr Asn Glu Ala Arg Ile
 65              70                  75                       80

Lys Val Ile Gly Val Gly Gly Gly Ser Asn Ala Val Asn Arg Met
             85                  90                  95

Ile Glu Ser Glu Met Ser Gly Val Glu Phe Trp Ile Val Asn Thr Asp
            100                 105                 110

Ile Gln Ala Met Arg Met Ser Pro Val Leu Pro Asp Asn Arg Leu Gln
            115                 120             125

Ile Gly Lys Glu Leu Thr Arg Gly Leu Gly Ala Gly Gly Asn Pro Glu
            130             135             140

Ile Gly Met Asn Ala Ala Arg Glu Ser Lys Glu Val Ile Glu Glu Ala
145             150             155                         160

Leu Tyr Gly Ser Asp Met Val Phe Val Thr Ala Gly Met Gly Gly Gly
                165             170             175

Thr Gly Thr Gly Ala Ala Pro Val Ile Ala Gly Ile Ala Lys Ala Met
            180             185             190

Gly Ile Leu Thr Val Gly Ile Ala Thr Thr Pro Phe Ser Phe Glu Gly
        195             200             205

Arg Arg Arg Thr Val Gln Ala Gln Glu Gly Leu Ala Ser Leu Arg Asp
210                 215                 220

Asn Val Asp Thr Leu Ile Val Ile Pro Asn Asp Lys Leu Leu Thr Ala
225             230                 235                 240

Val Ser Gln Ser Thr Pro Val Thr Glu Ala Phe Asn Leu Ala Asp Asp
                245                 250                 255

Ile Leu Arg Gln Gly Val Arg Gly Ile Ser Asp Ile Ile Thr Ile Pro
            260             265                 270

Gly Leu Val Asn Val Asp Phe Ala Asp Val Arg Ala Ile Met Ala Asn
            275             280             285

Ala Gly Ser Ser Leu Met Gly Ile Gly Thr Ala Thr Gly Lys Ser Arg
    290             295             300

Ala Arg Asp Ala Ala Leu Asn Ala Ile Gln Ser Pro Leu Leu Asp Ile
305             310             315                     320

Gly Ile Glu Arg Ala Thr Gly Ile Val Trp Asn Ile Thr Gly Gly Ser
                325             330             335

Asp Leu Thr Leu Phe Glu Val Asn Ala Ala Glu Val Ile Tyr Asp
            340             345             350

Leu Val Asp Pro Thr Ala Asn Leu Ile Phe Gly Ala Val Val Asp Pro
            355             360             365

Ala Leu Ser Gly Gln Val Ser Ile Thr Leu Ile Ala Thr Gly Phe Lys
    370             375             380

Arg Gln Glu Glu Gly Gly Arg Thr Val Gln Met Val Gln Ala Asp
385             390             395                     400

Ala Ala Ser Val Gly Ala Thr Arg Arg Pro Ser Ser Ser Phe Arg Glu
            405             410             415

Ser Gly Ser Val Glu Ile Pro Glu Phe Leu Lys Lys Lys Gly Ser Ser
            420             425             430

Arg Tyr Pro Arg Val
            435
```